United States Patent
O'Heeron et al.

(10) Patent No.: US 12,310,991 B2
(45) Date of Patent: May 27, 2025

(54) STIMULATION OF ANGIOGENESIS BY FIBROBLAST DERIVED EXOSOMES

(71) Applicant: SPINALCYTE LLC, Houston, TX (US)

(72) Inventors: Pete O'Heeron, Houston, TX (US); Thomas Ichim, San Diego, CA (US); Kristin Comella, Weston, FL (US)

(73) Assignee: Figene, LLC, Houston, TX (US)

( * ) Notice: Subject to any disclaimer, the term of this patent is extended or adjusted under 35 U.S.C. 154(b) by 0 days.

(21) Appl. No.: 16/495,371

(22) PCT Filed: Apr. 19, 2018

(86) PCT No.: PCT/US2018/028358
§ 371 (c)(1),
(2) Date: Sep. 18, 2019

(87) PCT Pub. No.: WO2018/195308
PCT Pub. Date: Oct. 25, 2018

(65) Prior Publication Data
US 2020/0338133 A1 Oct. 29, 2020

Related U.S. Application Data

(60) Provisional application No. 62/487,143, filed on Apr. 19, 2017.

(51) Int. Cl.
*A61K 35/33* (2015.01)
*A61P 17/02* (2006.01)
*C12N 5/077* (2010.01)

(52) U.S. Cl.
CPC .............. *A61K 35/33* (2013.01); *A61P 17/02* (2018.01); *C12N 5/0656* (2013.01); *C12N 2500/02* (2013.01); *C12N 2501/113* (2013.01); *C12N 2501/115* (2013.01)

(58) Field of Classification Search
None
See application file for complete search history.

(56) References Cited

U.S. PATENT DOCUMENTS

| | | |
|---|---|---|
| 2007/0184033 A1 | 8/2007 | Sevrain et al. |
| 2010/0216210 A1 | 8/2010 | Sevrain et al. |
| 2010/0285090 A1 | 11/2010 | Sevrain et al. |
| 2010/0285091 A1 | 11/2010 | Sevrain et al. |
| 2010/0285092 A1 | 11/2010 | Sevrain et al. |
| 2010/0285093 A1 | 11/2010 | Sevrain et al. |
| 2011/0275151 A1 | 11/2011 | Sevrain et al. |
| 2012/0093885 A1 | 4/2012 | Sahoo et al. |
| 2013/0195899 A1* | 8/2013 | Ichim .............. A61K 39/0008 424/184.1 |
| 2014/0044682 A1 | 2/2014 | O'Heeron |
| 2014/0314726 A1 | 10/2014 | O'Heeron et al. |
| 2014/0377231 A1 | 12/2014 | O'Heeron |
| 2015/0023908 A1 | 1/2015 | Al-Qahtani |
| 2015/0079046 A1 | 3/2015 | Sinden et al. |
| 2016/0145575 A1 | 5/2016 | Pimanda et al. |
| 2016/0213764 A1 | 7/2016 | Wagner et al. |
| 2016/0220613 A1 | 8/2016 | Lim |
| 2016/0220699 A1 | 8/2016 | O'Heeron |
| 2016/0243171 A1 | 8/2016 | Shiels et al. |
| 2017/0087277 A1 | 3/2017 | Sevrain et al. |
| 2018/0055887 A1 | 3/2018 | Lu et al. |
| 2018/0195044 A1 | 7/2018 | O'Heeron et al. |
| 2018/0236005 A1 | 8/2018 | O'Heeron et al. |
| 2018/0318466 A1 | 11/2018 | Sevrain et al. |
| 2019/0022145 A1 | 1/2019 | O'Heeron |
| 2019/0142871 A1 | 5/2019 | O'Heeron |
| 2021/0128636 A1 | 5/2021 | O'Heeron et al. |
| 2021/0154230 A1 | 5/2021 | O'Heeron et al. |

(Continued)

FOREIGN PATENT DOCUMENTS

| | | |
|---|---|---|
| CN | 104011201 | 8/2014 |
| WO | 2009/100029 A1 | 8/2009 |
| WO | WO 2010/138517 | 12/2010 |
| WO | 2015/179227 A1 | 11/2015 |
| WO | 2016/201323 A1 | 12/2016 |

OTHER PUBLICATIONS

Denu et al., Fibroblasts and Mesenchymal Stromal/Stem Cells are Phenotypically Indistinguishable, 2016, Acta Haematol, 136: 85-97.*
Soundarajan et al. Fibroblasts and mesenchymal stem cells: Two sidesof the same coin?, 2018, J Cellular Physiology, 233: 9099-9109.*
Shamis et al: "Fibroblasts Derived from Human Pluripotent Stem Cells Activate Angiogenic Responses in Vitro and in VivO", PLOS One, vol. 8, No. 12, Jan. 1, 2013 (Jan. 1, 2013), p. e83755.

(Continued)

*Primary Examiner* — Terry A McKelvey
*Assistant Examiner* — Catheryne Chen
(74) *Attorney, Agent, or Firm* — Norton Rose Fulbright US LLP (57) ABSTRACT

Disclosed are methods, means, and compositions of matter useful for the stimulation of angiogenesis directly by administration of membrane vesicles, such as fibroblast-derived exosomes, and/or through induction of angiogenic cytokines from blood cells contacted with fibroblast-derived exosomes. The invention provides means of treating conditions in which angiogenesis is beneficial through local or systemic administration of exosomes, including those derived from fibroblasts, wherein the fibroblasts are cultured under basal conditions or conditions of hypoxia. In other embodiments exosomes derived from fibroblasts are utilized to augment endogenous regenerative processes, such as hematopoiesis, angiogenesis and neurogenesis, as well as augment regenerative processes stimulated by administration of exogenous therapeutics such as cells, growth factors, or genes.

32 Claims, 2 Drawing Sheets

(56) References Cited

U.S. PATENT DOCUMENTS

| | | |
|---|---|---|
| 2021/0180020 A1 | 6/2021 | O'Heeron et al. |
| 2021/0230551 A1 | 7/2021 | O'Heeron et al. |
| 2021/0244769 A1 | 8/2021 | O'Heeron et al. |
| 2021/0393700 A1 | 12/2021 | O'Heeron et al. |

OTHER PUBLICATIONS

Wang, Y. et al: "Exosomes/microvesicles from induced pluripotent stem cells deliver cardioprotective miRNAs and prevent cardiomyocyte apoptosis in the ischemic myocardium", International Journal of Cardiology, vol. 192, May 8, 2015 (May 8, 2015), pp. 61-69, Elsevier, Amsterdam, NL.

Kato, T et al. "Exosomes from IL-1[beta] stimulated synovial fibroblasts induce osteoarthritic changes in articular chondrocytes", Arthritis Research & Therapy. Aug. 4, 2014, vol. 16, No. 4; pp. 1-11.

Webber, et al. "Cancer Exosomes Trigger Fibroblast to Myofibroblast Differentiation", Cancer Research. Dec. 1, 2010, Epub Nov. 23, 2010, vol. 70, No. 23.

English Translation of Office Action issued in corresponding Japanese Patent Application No. 2019-556899, dated Apr. 14, 2022.

Hu, Guo-Wen et al: "Exosomes secreted by human-induced pluripotent stem cell-derived mesenchymal stem cells attenuate limb ischemia by promoting angiogenesis in mice", Stem Cell Research & Therapy, vol. 6, No. 1, Apr. 10, 2015 (Apr. 10, 2015), p. 10, Biomed Central Ltd, London, UK.

Eckhard, Alt, et al; "Fibroblasts share mesenchymal phenotypes with stem cells, but lack their differentiation and colony-forming potential": Bio Cell, Apr. 2011: 103 (4):197-208.

Balducci et al., "The differences between mesenchymal stromal cells and fibroblasts"; Chapter 30, The Biology and Therapeutic Application of Mesenchymal Cells: The Cellular and Molecular Biology of Mesenchymal Stromal Cells, John Wiley and Sons, 2016.

Lamparski et al., "Production and characterization of clinical grade exosomes derived from dendritic cells," Journal of Immunological Methods, 2002, 270:211-226.

Office Communication issued in Chinese Patent Application No. 201880025815.1, dated Oct. 24, 2023.

Anokye-Danso et al., "Highly Efficient miRNA-Mediated Reprogramming of Mouse and Human Somatic Cells to Pluripotency," Cell Stem Cell, 8:376-388, 2011.

Cheng et al., "Mesenchymal stem cells deliver exogenous miR-21 via exosomes to inhibit nucleus pulposus cell apoptosis and reduce intervertebral disc degeneration," Journal of Cellular and Molecular Medicine, 22(1):261-276, 2018.

Collas et al., "On the way to reprogramming cells to pluripotency using cell-free extracts," Reproductive BioMedicine Online, 12(6):762-770, 2006.

Extended European Search Report issued in European Patent Application No. 19795797.0, dated Oct. 21, 2021.

Im et al., "Repair of cartilage defect in the rabbit with cultured mesenchymal stem cells from bone marrow," J. Bone Joint Surg., 83-B:289-94, 2001.

Jung et al., "Reprogram or Reboot: Small Molecule Approaches for the Production of Induced Pluripotent Stem Cells and Direct Cell Reprogramming," ACS Chemical Biology, 9:80-95, 2014.

Lai et al., "Efficient Generation of Chemically Induced Mesenchymal Stem Cells from Human Dermal Fibroblasts," Scientific Reports, 7:44534, doi: 10.1038/srep44534, 2017.

Mathieu et al., "Hypoxia-inducible Factors Have Distinct and Stage-Specific Roles during Reprogramming of Human Cells to Pluripotency," Cell Stem Cell, 14:592-605, 2014.

Obokata et al., "Stimulus-triggered fate conversion of somatic cells into pluripotency," Nature, including Extended Data and Retraction, 505:641-647, 2014.

Office Communication issued in U.S. Appl. No. 17/052,841, dated Jul. 19, 2023.

Elston et al., "Skin biopsy," J. Am. Acad. Dermatol., 74(1):1-16, 2016.

Kirschner et al., "Oxygen, " Ullmann's Encyclopedia of Industrial Chemistry, pp. 1-32, 2017.

Liu et al., "Mouse embryonic fibroblast (MEF)/BMP4-conditioned medium enhanced multipotency of human dental pulp cells," Journal of Molecular History, 49:17-26, 2018.

Office Communication issued in U.S. Appl. No. 18/345,022, dated Mar. 12, 2024.

Salci et al., "Acquisition of pluripotency through continued environmental influence on OCT4-induced plastic human fibroblasts," Stem Cell Research, 15:221-230, 2015.

Van Der Valk et al., "Fetal Bovine Serum (FBS): Past-Present-Future," Altex, 35(1):99-118, 2018.

Arora, "Cell Culture Media: A Review," Mater. Methods, 3(175):1-29, 2013.

Cell Guidance System, "Conditioning cell culture media," retrieved from the internet at www.cellgs.com/blog/conditioning-cell-culture-media.html, 5 pages, 2020.

Cheng et al., "Generation of neural progenitor cells by chemical cocktails and hypoxia," Cell Research, 24:665-679, 2014.

Jeong et al., "Effect of Concentrated Fibroblast-Conditioned Media on In Vitro Maintenance of Rat Primary Hepatocyte," PLoS ONE, 11(2):e0148846, pp. 1-14, 2016.

Kalluri and Lebleu, "The biology, function, and biomedical applications of exosomes," Science, 367:1-15, 2020.

Office Communication issued in U.S. Appl. No. 18/345,022, dated Sep. 25, 2024.

Satoh et al., "Regulation of dermal fibroblast dedifferentiation and redifferentiation during wound healing and limb regeneration in the Axolotl," Develop. Growth Differ., 50:743-754, 2008.

Defendi-Chi and Gould, "In vitro culture of bovine fibroblasts using select serum-free media supplemented with Chlorella vulgaris extract," BMC Biotechnology, 23(4): 1-11, 2023.

Ejiri et al., "Use of synthetic serum-free medium for culture of human dermal fibroblasts to establish an experimental system similar to living dermis," Cytotechnology, 67(3):507-514, 2015.

Merriam-Webster, "Dedifferentiation," definition. Available at https://www.merriam-webster.com/dictionary/dedifferentiation?utm_campaign=sd&utm_medium=serp&utm_source=jsonld. 1 page. Accessed Oct. 23, 2024.

Office Communication issued in U.S. Appl. No. 17/052,841, dated Nov. 5, 2024.

Pilkus et al., "Fibroblasts: origins definitions, and functions in health and disease," Cell, 184(15):3852-3872, 2021.

ThermoFisher, "Human Fibroblast Expansion Medium (formerly "Medium 106) User Guide. Available at https://assets.fishersci.com/TFS-Assets/LSG/manuals/M106_man.pdf. 2 pages. Accessed Oct. 23, 2024.

ThermoFisher, Low Serum Growth Supplement (LSGS) User Guide. Available at https://assets.fishersci.com/TFS-Assets/LSG/manuals/LSGS_LSGS_Kit_man.pdf. 1 page. Accessed Oct. 23, 2034.

Yoshida et al., "Hypoxia Enhances the Generation of Induced Pluripotent Stem Cells," Cell Stem Cell, 5:237-241, 2009.

Huangfu et al., "Induction of pluripotent stem cells by defined factors is greatly improved by small molecule compounds," Nat. Biotechnol., 26(7):795-797, 2008.

* cited by examiner

STIMULATION OF ANGIOGENESIS BY FIBROBLAST DERIVED EXOSOMES

The present application is a national phase application under 35 U.S.C. § 371 that claims priority to International Application No. PCT/US2018/028358 filed Apr. 19, 2018, which claims priority to U.S. Provisional Patent Application Ser. No. 62/487,143, filed Apr. 19, 2017, both of which are incorporated by reference herein in their entirety.

TECHNICAL FIELD

Embodiments of the present disclosure include at least the fields of cell biology, molecular biology, physiology, and medicine.

BACKGROUND OF THE INVENTION

Figure 1:
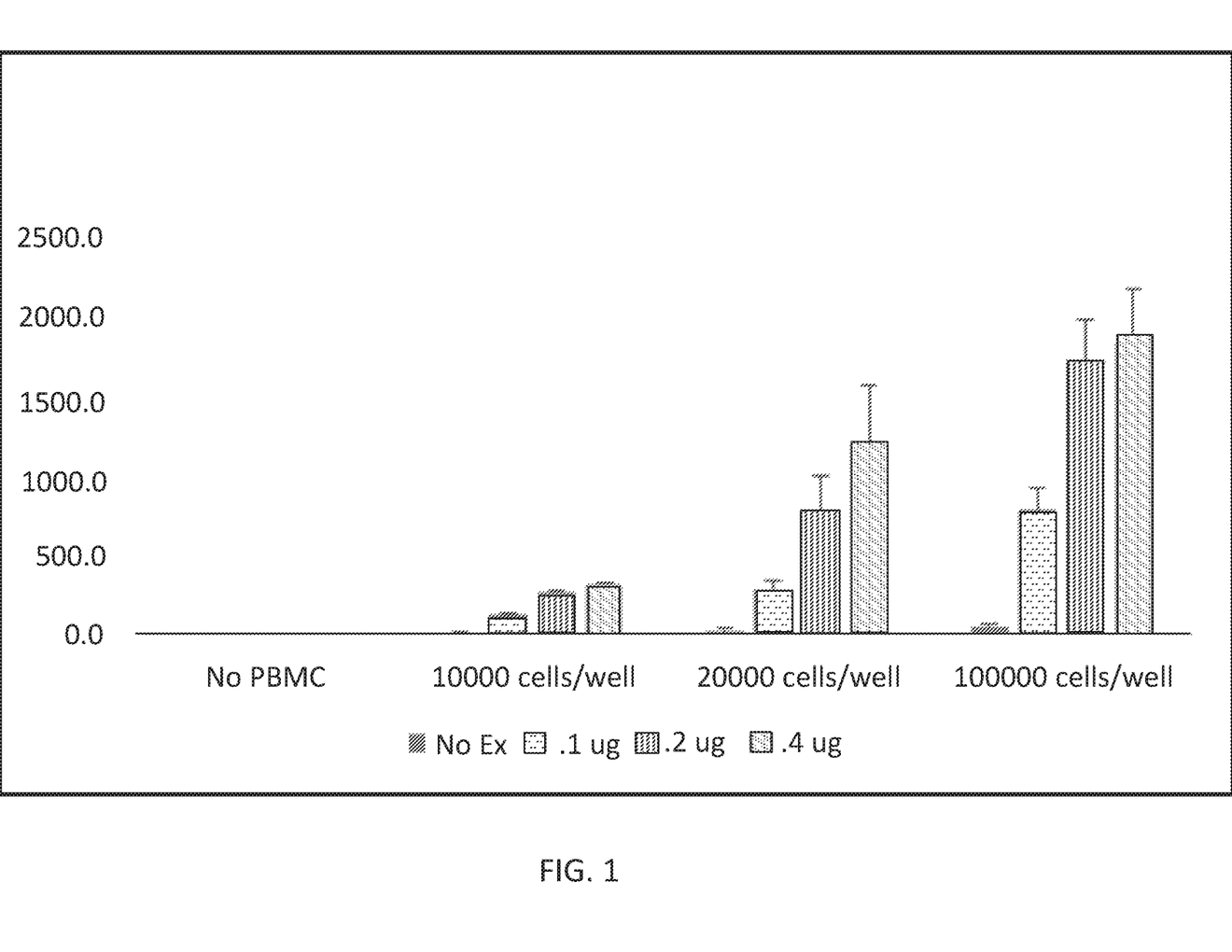
FIG. 1 shows stimulation of VEGF from PBMCs by fibroblast-derived exosomes.

Exosomes are nanoparticles (40-100 nm) in size that possess highly defined homogeneous characteristics [1]. Exosomes are different from microvesicles, which are released in a non-specific manner (FIG. 1). Originally, thought to be a by-product of cell protein turnover [2], these nanoparticles are becoming appreciated as a critical means of intracellular communication in areas ranging from neurotransmission [3], to immune modulation [2], to infectious disease [4]. Compared with other secreted vesicles, exosomes have much better defined biophysical and biochemical properties, specifically, they have a diameter of 40-100 nm (with a density in sucrose of 1.13-1.19 g/ml, and they can be sedimented at 100,000 g [1]. Their membranes are enriched in cholesterol, sphingomyelin and ceramide, and they are known to contain lipid rafts. Exosomes were originally discovered as a means of exportation of the transferrin receptor during sheep reticulocyte maturation [5]. In recent years, an explosion of interest in exosomes has occurred, with a wide variety of cells being reported to secrete these nanoparticles ranging from T cells [6, 7], B cells [8, 9], dendritic cells [10, 11], tumor cells [12, 13], neurons [14, 15], oligodendrocytes [16], and placental cells [17].

The present disclosure at least provides solutions to long-felt needs in the art of therapy using exosomes.

BRIEF SUMMARY OF THE INVENTION

Embodiments of the disclosure concern the unexpected finding that membrane vesicles, such as exosomes, possess therapeutic properties. Although in some cases the therapeutic property can be of any kind, in specific cases the membrane vesicle comprises properties for angiogenesis, hematopoiesis, and/or neurogenesis stimulation. Although the source of membrane vesicle may be of any source, in specific embodiments the source of exosome is from a mammalian cell. In specific embodiments, the membrane vesicle is derived from one or more types of fibroblasts. In specific embodiments, membrane vesicles are utilized to deliver one or more therapeutic signals from one or more types of cells. In at least certain cases, the membrane vesicles allow for leveraging the benefits of a cell therapy without the drawbacks of needing to store and deliver actual cells, for example.

Specific embodiments of the disclosure pertain to the field of angiogenesis stimulation, including to the use of conditioned media for stimulation of angiogenesis, for example. In specific embodiments, the disclosure encompasses the use of membrane vesicles generated from fibroblast-conditioned media for any therapeutic and/or preventative application, including at least the stimulation of angiogenesis.

Examples of embodiments include methods of stimulating angiogenesis in an individual, comprising the step of administering to the individual an effective amount of fibroblast-derived exosomes or one or more biologically active fractions thereof. An exosome may be considered to be fibroblast-derived if it is obtained from the culture of fibroblasts, as an example. The media of the culture may be specifically manipulated for the purpose of producing exosomes having one or more characteristics, for example, the media may comprise one or more factors that are mitogenic for fibroblasts.

In one embodiment, there is a method of stimulating angiogenesis in an individual, comprising the steps of: a) obtaining one or more fibroblast cells; b) culturing said fibroblast cells in a culture under conditions to allow for production of exosomes into culture media; c) extracting exosomes from said culture media; and d) administering said extracted exosomes or one or more biologically active fractions thereof (that is, able to stimulate angiogenesis) into an individual in need of angiogenesis, including therapeutic angiogenesis. An individual in need of angiogenesis may be an individual at risk for limb loss, an individual in need of prevention of limb loss, an individual with or at risk for cardiovascular disease or coronary artery disease, and so forth. The individual may have one or more underperfused tissues and/or organs. Tissues and/or organs in need of angiogenesis may be of any kind, including muscle, skin, vessels, cartilage, heart, brain, stomach, duodenum, intestine, pancreas, spleen, uterus, kidney, liver, and so forth. The individual may have an ischemic disease (for example, ischemic heart disease or ischemic brain disease (stroke)), including one that develops because of deficient angiogenesis. The individual may require post-stroke healing. The individual may have gastrointestinal ulceration, such as a duodenal ulcer. In cases wherein the individual has coronary artery disease, the coronary artery disease may not be amenable to complete revascularization by medical intervention, such as percutaneous transluminal coronary angioplasty and/or coronary artery bypass grafting. The individual may be in need of wound healing of any kind. As an example, the individual may have diabetes and, in some cases, as part of the diabetes they have insufficient wound healing.

In specific cases, the fibroblasts are derived from a biopsy. The fibroblasts may or may not be from the individual. The fibroblasts may be cultured in a media allowing for fibroblast proliferation, for example media that comprises one or more factors that are mitogenic for fibroblasts. Examples of factors that are mitogenic for fibroblasts include one or more factors selected from the group comprising of: a) FGF-1; b) FGF-2; c) FGF-5; d) EGF; e) CNTF; f) KGF-1; g) PDGF; h) platelet rich plasma; i) TGF-alpha; j) HGF-1; and (k) a combination thereof.

In specific embodiments, the fibroblasts are cultured under hypoxia. The exosomes may be collected from fibroblasts while said fibroblasts are in a proliferating state. In some cases, the exosomes are collected from fibroblasts while the fibroblasts are cultured in a media comprising no proliferation-inducing factors or in media that comprise reduced levels of the proliferation-inducing growth factors (compared to standard levels). In particular embodiments, exosomes are collected from said fibroblasts that have been cultured in 2-8% oxygen for at least 1 day, such as for 1-15 days or for 5-10 days, for example. In specific embodiments, the cells are passaged for at least 1 passage.

In particular embodiments, the exosomes are in a preparation, and the preparation may comprise less than 5% polyethylene glycol. The exosomes may be purified using polyethylene glycol and/or purified using ultrafiltration. The polyethylene glycol may be added to the exosomes after purification.

In particular embodiments, the exosomes express markers selected from a group consisting of (a) CD63; (b) CD9; (c) MHC I; (d) CD56; and (e) a combination thereof. The fibroblasts may be cultured in a media selected from the group consisting of a) Roswell Park Memorial Institute (RPMI-1640); b) Dulbecco's Modified Essential Media (DMEM), c) Eagle's Modified Essential Media (EMEM), d) Optimem, e) Iscove's Media, and f) a combination thereof. In particular embodiments, during extraction and/or following extraction, the exosomes are selected for based on one or more of expressed markers by the exosomes, including those listed above, as examples.

In methods including an extracting step, the extracting step may comprise anion exchange chromatography under high pressure. The support for the anion exchange chromatography may be functionalized with quaternary amines. The support for the anion exchange chromatography may be in the form of beads, for example. In specific cases, the extracting step comprises gel permeation chromatography, which may occur before or after the anion exchange chromatography. In specific cases, the extracting step further comprises an enrichment step for the exosomes. Such an enrichment step may comprise one or more of centrifugation, clarification, filtration, concentration, and/or ultrafiltration. In particular cases, the extracting step further comprises non-specific affinity chromatography. The extracting step may further comprise filtration.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the invention may consist of or consist essentially of one or more elements, method steps, and/or methods of the invention. It is contemplated that any method or composition described herein can be implemented with respect to any other method or composition described herein.

The term "exosome" as used herein refers to small membrane vesicles of endocytic origin that are secreted by cells in culture, such as fibroblasts.

II. General Embodiments of the Disclosure

The disclosure encompasses therapy for an individual with a medical condition or at risk for a medical condition by providing an effective amount of exosomes that improve at least one symptom of the medical condition, for example. In specific embodiments, the medical condition is one in which stimulation of angiogenesis would be therapeutic. Thus, in at least certain cases the disclosure provides means of stimulating angiogenesis using exosomes. The exosomes may be of any source, including those derived from fibroblasts. The fibroblasts may or may not be present in tissue cultures.

In one embodiment, the disclosure encompasses methods for the extraction of exosomes from cultures of fibroblasts and this may also include the concentration of the exosomes and administration of the exosomes, including for the purpose of stimulating angiogenesis. Without being bound by theory, the exosomes produced by the tissue culture may stimulate angiogenesis through directly acting as mitogens for endothelial cells and/or may stimulate angiogenesis by inducing production of pro-angiogenic cytokines in cells of the body, for example, in cells of the blood. In certain embodiments, such mechanisms are not involved.

In one embodiment, fibroblasts are cultured for preserving viability and proliferative ability of fibroblasts. The disclosure may be applied both for individualized autologous exosome preparations and for exosome preparations obtained from one or more other individuals, including established cell lines for experimental or biological or therapeutic use, for example. In one embodiment, the disclosure encompasses use of chromatography separation methods for preparing membrane vesicles, particularly to separate the membrane vesicles from potential biological contaminants, wherein the microvesicles may be exosomes, and wherein cells utilized for generating the exosomes are fibroblast cells. Methods of preparing exosomes from fibroblasts for a therapeutic use are encompassed in the disclosure.

As shown herein, membrane vesicles, particularly exosomes, can be purified that possess the ability to stimulate angiogenesis. In one embodiment, a strong or weak anion exchange may be performed, although in specific embodiments it is a strong anion exchange. In addition, in a specific embodiment the chromatography is performed under pressure. Thus, more specifically, it may comprise high performance liquid chromatography (HPLC).

In cases wherein anion exchange chromatography is employed, different types of supports may be used to perform the anion exchange chromatography. In particular embodiments, these include cellulose, poly(styrene-divinylbenzene), agarose, dextran, acrylamide, silica, ethylene glycol-methacrylate co-polymer, or mixtures thereof, e.g., agarose-dextran mixtures. In some cases, particular chromatography equipment comprised of supports, and particularly the following gels, may be utilized: SOURCE. POROS®, SEPHAROSE®, SEPHADEX®, TRISACRYL®, TSK-GEL SW OR PW®, SUPERDEX®, TOYOPEARL HW and SEPHACRYL®. Therefore, in a specific embodiment, this disclosure relates to a method of preparing membrane vesicles, particularly exosomes, from a biological sample such as a tissue culture comprising fibroblasts, comprising at least one step during which the biological sample is treated by anion exchange chromatography on a support, including (for example) one selected from cellulose, poly(styrene-divinylbenzene), silica, acrylamide, agarose, dextran, ethylene glycol-methacrylate co-polymer, alone or in mixtures, and in optional cases the support is functionalized.

In addition, to improve the chromatographic resolution, within the scope of the disclosure, it is useful in specific embodiments to use supports in bead form. In particular embodiments, these beads have a homogeneous and calibrated diameter, with a sufficiently high porosity to enable the penetration of the objects under chromatography (i.e., the exosomes). In this way, given the diameter of exosomes (generally between 50 and 100 nm), to apply the teachings of this disclosure, one may use high porosity gels, particularly between 10 nm and 5 µm, such as between approximately 20 nm and approximately 2 µm, including between about 100 nm and about 1 µm, for example. For the anion exchange chromatography, the support used may be functionalized using a group capable of interacting with an anionic molecule. Generally, this group is comprised of an amine that may be ternary or quaternary, which defines a weak or strong anion exchanger, respectively. Within the scope of this disclosure, it is useful to use a strong anion exchanger. In this way, according to the disclosure, a chromatography support as described above, functionalized with quaternary amines, for example, is used. Therefore, according to a more specific embodiment of the invention, the anion exchange chromatography is performed on a support functionalized with a quaternary amine. In at least some cases, this support is selected from poly(styrene-divinylbenzene), acrylamide, agarose, dextran and silica, alone or in mixtures, and functionalized with a quaternary amine Examples of supports functionalized with a quaternary amine include the gels SOURCEQ. MONO Q, Q SEPHAROSE®, POROS® HQ and POROS® QE, FRACTOGEL® TMAE type gels and TOYOPEARL SUPER® Q gels.

In particular embodiments, a support to perform the anion exchange chromatography comprises poly(styrene-divinylbenzene). An example of this type of gel that may be used within the scope of this disclosure is SOURCE Q gel, particularly SOURCE 15 Q (Pharmacia). This support offers the advantage of having very large internal pores, thus offering low resistance to the circulation of liquid through the gel, while enabling rapid diffusion of the exosomes to the functional groups, which are useful parameters for exosomes given their size. The biological compounds retained on the column may be eluted in one or more ways, particularly using the passage of a saline solution gradient of increasing concentration, e.g. from 0 to 2 M. A sodium chloride solution may particularly be used, in concentrations varying from 0 to 2 M, for example. The different fractions purified in this way are detected by measuring their optical density (OD) at the column outlet using a continuous spectro-photometric reading. As an indication, under the conditions used in the examples, the fractions comprising the membrane vesicles were eluted at an ionic strength comprised between approximately 350 and 700 mM, depending on the type of vesicles.

Different types of columns may be used to perform this chromatographic step, according to requirements and the volumes to be treated. For example, depending on the preparations, it is possible to use a column from approximately 100 µl up to 10 ml or greater. In this way, the supports available have a capacity that may reach 25 mg of proteins/ml, for example. For this reason, a 100 µl column has a capacity of approximately 2.5 mg of proteins which, given the samples in question, allows the treatment of culture supernatants of approximately 2 l (which, after concentration by a factor of 10 to 20, for example, represent volumes of 100 to 200 ml per preparation). It is understood that higher volumes may also be treated, by increasing the volume of the column, for example. In addition, to perform at least certain methods of this disclosure, it is also possible to combine the anion exchange chromatography step with a gel permeation chromatography step. In this way, according to a specific embodiment of the disclosure, a gel permeation chromatography step is added to the anion exchange step, either before or after the anion exchange chromatography step. In particular cases, in this embodiment, the permeation chromatography step takes place after the anion exchange step. In addition, in a specific variant, the anion exchange chromatography step is replaced by the gel permeation chromatography step. The present disclosure demonstrates that membrane vesicles may also be purified using gel permeation liquid chromatography, particularly when this step is combined with an anion exchange chromatography or other treatment steps of the biological sample, as described in detail below.

To perform the gel permeation chromatography step, a support selected from silica, acrylamide, agarose, dextran, ethylene glycol-methacrylate co-polymer or mixtures thereof, e.g., agarose-dextran mixtures, may be used. As an illustration, for gel permeation chromatography, a support such as SUPERDEX®200HR (Pharmacia), TSK G6000 (TosoHaas) or SEPHACRYL® S (Pharmacia) may be used.

The processes according to the disclosure may be applied to one or more different biological samples. In particular, these may comprise a biological fluid from a subject (bone marrow, peripheral blood, etc.), a culture supernatant, a cell lysate, a pre-purified solution or any other composition comprising membrane vesicles.

In this respect, in a specific embodiment of the disclosure, the biological sample is a culture supernatant of membrane vesicle-producing fibroblast cells.

In addition, according to a certain embodiment of the invention, the biological sample is treated prior to a chromatography step, for example to be enriched with membrane vesicles (enrichment stage). In this way, in a specific embodiment, this disclosure relates to a method of preparing membrane vesicles from a biological sample, characterized in that it comprises at least: a) an enrichment step, to prepare a sample enriched with membrane vesicles, and b) a step during which the sample is treated by anion exchange chromatography and/or gel permeation chromatography.

In one embodiment, the biological sample is a culture supernatant treated so as to be enriched with membrane vesicles. In particular, the biological sample may be composed of a pre-purified solution obtained from a culture supernatant of a population of membrane vesicle-producing cells or from a biological fluid, by treatments such as centrifugation, clarification, ultrafiltration, nanofiltration and/or affinity chromatography, particularly with clarification and/or ultrafiltration and/or affinity chromatography. Therefore, a particular method of preparing membrane vesicles according to this disclosure may comprise the following steps: a) culturing a population of membrane vesicle (e.g. exosome) producing cells under conditions enabling the release of vesicles, b) a step of enrichment of the sample in membrane vesicles, and c) an anion exchange chromatography and/or gel permeation chromatography treatment of the sample.

As indicated above, the sample (e.g. supernatant) enrichment step may comprise one or more of centrifugation, clarification, ultrafiltration, nanofiltration and/or affinity chromatography steps on the supernatant. In a first specific embodiment, the enrichment step comprises (i) the elimination of cells and/or cell debris (clarification), possibly followed by (ii) a concentration and/or affinity chromatography step. In another specific embodiment, the enrichment step comprises an affinity chromatography step, optionally preceded by a step of elimination of cells and/or cell debris (clarification). A particular enrichment step according to this disclosure comprises (i) the elimination of cells and/or cell debris (clarification), (ii) a concentration and (iii) an affinity chromatography. The cells and/or cell debris may be eliminated by centrifugation of the sample, for example, at a low speed, preferably below 1000 g, between 100 and 700 g, for example. Preferred centrifugation conditions during this step are approximately 300 g or 600 g for a period between 1 and 15 minutes, for example.

The cells and/or cell debris may also be eliminated by filtration of the sample, possibly combined with the centrifugation described above. The filtration may particularly be performed with successive filtrations using filters with a decreasing porosity. For this purpose, filters with a porosity above 0.2 µm, e.g. between 0.2 and 10 µm, may be used. It is particularly possible to use a succession of filters with a porosity of 10 µm, 1 µm, 0.5 µm followed by 0.22 µm.

A concentration step may also be performed, for example in order to reduce the volumes of sample to be treated during the chromatography stages. In this way, the concentration may be obtained by centrifugation of the sample at high speeds, e.g. between 10,000 and 100,000 g, to cause the sedimentation of the membrane vesicles. This may comprise a series of differential centrifugations, with the last centrifugation performed at approximately 70,000 g. The membrane vesicles in the pellet obtained may be taken up with a smaller volume and in a suitable buffer for the subsequent steps of the process. The concentration step may also be performed by ultrafiltration. In fact, this ultrafiltration allows both to concentrate the supernatant and perform an initial purification of the vesicles. According to a certain embodiment, the biological sample (e.g., the supernatant) is subjected to an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibres (Amicon, Millipore, Sartorius, Pall, GF, Sepracor). Within the scope of the disclosure, the use of membranes with a cut-off threshold below 1000 kDa, or which may be between 300 kDa and 1000 kDa, or even which may be between 300 kDa and 500 kDa, is advantageous.

The affinity chromatography step may be performed in various ways, using different chromatographic support and material. In particular embodiments, the chromatography is a non-specific affinity chromatography, aimed at retaining (i.e., binding) certain contaminants present within the solution, without retaining the objects of interest (i.e., the exosomes). It is therefore a negative selection. In some embodiments, an affinity chromatography on a dye is used, allowing the elimination (i.e., the retention) of contaminants such as proteins and enzymes, for instance albumin, kinases, deshydrogenases, clotting factors, interferons, lipoproteins, or also co-factors, etc. In certain cases, the support used for this chromatography step is a support as used for the ion exchange chromatography, functionalized with a dye. As specific example, the dye may be selected from Blue SEPHAROSE® (Pharmacia), YELLOW 86, GREEN 5 and BROWN 10 (Sigma). The support is more preferably agarose. It should be understood that any other support and/or dye or reactive group allowing the retention (binding) of contaminants from the treated biological sample can be used in the instant disclosure.

In one embodiment, a membrane vesicle preparation process within the scope of this disclosure comprises the following steps: a) the culture of a population of membrane vesicle (e.g. exosome) producing cells under conditions enabling the release of vesicles, b) the treatment of the culture supernatant with at least one ultrafiltration or affinity chromatography step, to produce a biological sample enriched with membrane vesicles (e.g. with exosomes), and c) an anion exchange chromatography and/or gel permeation chromatography treatment of the biological sample. In a particular embodiment, step b) above comprises a filtration of the culture supernatant, followed by an ultrafiltration, preferably tangential. In another embodiment, step b) above comprises a clarification of the culture supernatant, followed by an affinity chromatography on dye, preferably on Blue SEPHAROSE®.

In addition, after step c), the material harvested may, if applicable, be subjected to one or more additional treatment and/or filtration stages d), particularly for sterilization purposes. For this filtration treatment stage, filters with a diameter less than or equal to 0.3 µm are preferentially used, or even more preferentially, less than or equal to 0.25 µm. Such filters have a diameter of 0.22 µm, for example.

After step d), the material obtained is, for example, distributed into suitable devices such as bottles, tubes, bags, syringes, etc., in a suitable storage medium. The purified vesicles obtained in this way may be stored cold, frozen or used extemporaneously. Therefore, a specific preparation process within the scope of the invention comprises at least the following steps: c) an anion exchange chromatography and/or gel permeation chromatography treatment of the biological sample, and d) a filtration step, particularly sterilizing filtration, of the material harvested after stage c). In a first variant, the process according to the disclosure comprises: c) an anion exchange chromatography treatment of the biological sample, and d) a filtration step, particularly sterilizing filtration, on the material harvested after step c).

In another variant, the process according to the disclosure comprises: c) a gel permeation chromatography treatment of the biological sample, and d) a filtration step, particularly sterilizing filtration, on the material harvested after step c). According to a third variant, the process according to the invention comprises: c) an anionic exchange treatment of the biological sample followed or preceded by gel permeation chromatography, and d) a filtration step, particularly sterilizing filtration, on the material harvested after step c).

Further embodiments include a method of optimizing angiogenesis stimulating therapeutic factor production from fibroblast cultures through the use of filters that separate compositions based on electrical charge, size or ability to elute from an adsorbent. Numerous techniques are known in the art for purification of therapeutic factors and concentration of said agents. For some particular uses the fibroblast derived compounds will be sufficient for use as culture supernatants of said cells in media. Currently media useful for this purpose include Roswell Park Memorial Institute (RPMI-1640), Dulbecco's Modified Essential Media (DMEM), Eagle's Modified Essential Media (EMEM), Optimem, and Iscove's Media.

In one embodiment, therapeutic factors for stimulating angiogenesis are derived from tissue culture that may comprise exosomes, or may not comprise exosomes but comprise factors capable of stimulating angiogenesis. In such as embodiment, culture conditioned media may be concentrated by filtering/desalting means known in the art including use of Amicon filters with specific molecular weight cut-offs, said cut-offs may select for molecular weights higher than 1 kDa to 50 kDa. Supernatant may alternatively be concentrated using means known in the art such as solid phase extraction using C18 cartridges (Mini-Spe-ed C18-14%, S.P.E. Limited, Concord ON). The cartridges are prepared by washing with methanol followed by deionized-distilled water. Up to 100 ml of fibroblast conditioned media supernatant may be passed through each of these specific cartridges before elution, it is understood of one of skill in the art that larger cartridges may be used. After washing the cartridges material adsorbed is eluted with 3 ml methanol, evaporated under a stream of nitrogen, redissolved in a small volume of methanol, and stored at 4° C. Before testing the eluate for activity in vitro, the methanol is evaporated under nitrogen and replaced by culture medium. The C18 cartridges are used to adsorb small hydrophobic molecules from the fibroblast conditioned supernatant, and allows for the elimination of salts and other polar contaminants. It may, however be desired to use other adsorption means in order to purify certain compounds from the supernatant. The concentrated supernatant may be assessed directly for biological activities useful for the practice of this invention, or may be further purified. Further purification may be performed using, for example, gel filtration using a Bio-Gel P-2 column with a nominal exclusion limit of 1800 Da (Bio-Rad, Richmond Calif.). The column may be washed and pre-swelled in 20 mM Tris-HCl buffer, pH 7.2 (Sigma) and degassed by gentle swirling under vacuum. Bio-Gel P-2 material be packed into a 1.5×54 cm glass column and equilibrated with 3 column volumes of the same buffer. Fibroblast cell supernatant concentrates extracted by C18 cartridge may be dissolved in 0.5 ml of 20 mM Tris buffer, pH 7.2 and run through the column Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry. Administration of supernatant active fractions may be performed locally or systemically.

Included in the disclosure are methods of treating an individual for risk of limb loss, ischemic heart disease, ischemic brain disease, gastrointestinal ulcer, and/or one or more wounds by providing to the individual an effective amount of fibroblast-derived exosomes or one or more biologically active fractions thereof. A fraction may be determined to be biologically active using routine methods in the art of establishing fractions of a starting material and testing for a particular active with each fraction. In specific cases of the disclosure, the activity to be tested may be production of one or more particular compounds, such as one or more factors, for example VEGF. In additional or other cases the fractions may be tested in an in vivo model, such as an in vivo mouse model for limb loss.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fibroblast Exosomes Stimulate VEGF Production

In one embodiment of the invention, exosomes generated from fibroblasts are used for "Angiogenesis Therapy". Angiogenesis therapy has been described as a "biological bypass", the idea being that through administration of agents capable of inducing collateralization, a more natural type of "bypass" can be achieved. Indeed, it has been observed that ischemic muscles secrete angiogenic factors in response to hypoxia and that to some extent natural angiogenesis does occur in animal models of critical limb ischemia (CLI) and in humans (15, 16). Thus by augmenting these natural processes, researchers have attempted to prevent amputation. One of the angiogenic factors noted in many ischemic conditions, including cardiac ischemia, stroke, and CLI is vascular endothelial growth factor (VEGF) (17-19). In 1994, limb salvage and increased angiogenesis was reported in a rabbit CLI model after single bolus intra-arterial administration of VEGF-165 (20). Other experiments in the same model demonstrated no incidence of calf muscle atrophy and distal limb necrosis, whereas this was present in 85.7% of control rabbits, after VEGF administration (21, 22). A variety of studies have repeated these findings in other models of CLI (23-25). Unfortunately, this was not successfully reproduced in the clinic. Trials using VEGF protein (26), or DNA plasmid, did not show significant benefit at reducing leg amputations in a double blind setting (25, 27). In one embodiment of the invention, exosomes derived from fibroblasts are utilized to stimulate VEGF production from cells of the patient.

Another approach involved use of the cytokine fibroblast growth factor-1 (FGF-1). Given that FGF-1 is considered "upstream" of VEGF, it was believed to stimulate numerous angiogenic processes so as to result in creation of more mature vessels (28). FGF, like VEGF, is part of the natural tissue response to hypoxia, as demonstrated both in animal models (29) and clinical trials (30). The critical role of FGF in endogenous angiogenesis was conclusively demonstrated in FGF conditional knockout mice, which displayed inhibited ability to heal post-wounding or to form neovascularization (31). Although FGF-1 gene therapy has clinically been used in CLI patients with some improvement in ABI and perfusion, results were mediocre (32). Attempts at replicating the in vivo angiogenic cascade by combination of cytokines yielded more promising results. Cao et al demonstrated synergy between administration of PDGF-BB and FGF-2 in terms of increasing blood vessel formation and function in the femoral artery ligation model in rats and rabbits (33). Similarly, in cancer angiogenesis, it is known that several tumor-derived angiogenic factors synergize for acceleration of neovascularization (34). Investigators have attempted to activate upstream mediators of several angiogenic signals through transfection of genes encoding transcription factors such as HIF-1 alpha (35). In fact, this approach has been demonstrated to be superior to VEGF gene administration in terms of new capillary sprouting. In a Phase I dose-escalating trial, transfection of HIF-1 alpha into CLI patients demonstrated tolerability with some indication of efficacy (36). In conclusion, while administration of angiogenic factors to patients with CLI does induce some benefit in early trials, data from randomized trials to date do not support widespread use. The transfection of upstream transcription factors such as HIF-1 alpha is a promising approach since it mimics natural angiogenesis in that a plurality of growth factors are induced following transfection (35, 37). In another embodiment of the invention, the use of fibroblast derived exosomes for enhancement of cytokine and other angiogenic therapies is disclosed.

Exosomes were prepared from the cell culture supernatant of day 4 foreskin fibroblast cultures by differential centrifugation. Briefly, recovered culture supernatant was subjected to three successive centrifugations at 300 g (5 min), 1,200 g (20 min), and 10,000 g (30 min) to eliminate cells and debris, followed by centrifugation for 1 h at 100,000 g. To remove excess serum proteins, the exosome pellet was washed with a large volume of PBS, centrifuged at 100,000 g for 1 h, and finally resuspended in 120 µl of PBS for further studies. The exosomes were quantified by a micro Bradford protein assay (Bio-Rad). Each batch was standardized by protein content.

Peripheral blood mononuclear cells (PBMC) were isolated from 5 ml of blood by Ficoll density gradient (Sigma-Aldrich). Cells were washed twice in phosphate buffered saline (PBS) and plated in round-bottom, 96-well plates (Nunc). In each well, 10,000, 20,000 or 100,000 PBMC where added to a total volume of 200 µL in RPMI media containing 10% fetal calf serum (Life Technologies). Exosomes were added at concentrations of 0.1 µg/ml, 0.2 µg/ml and 0.4 µg/ml. Cells were cultured for 48 hours and concentration of VEGF was analyzed by ELISA (R&D Systems). Concentrations were expressed as pg/ml in FIG. 1.

Example 2

Fibroblast Exosomes Stimulate HUVEC Proliferation

Figure 2:
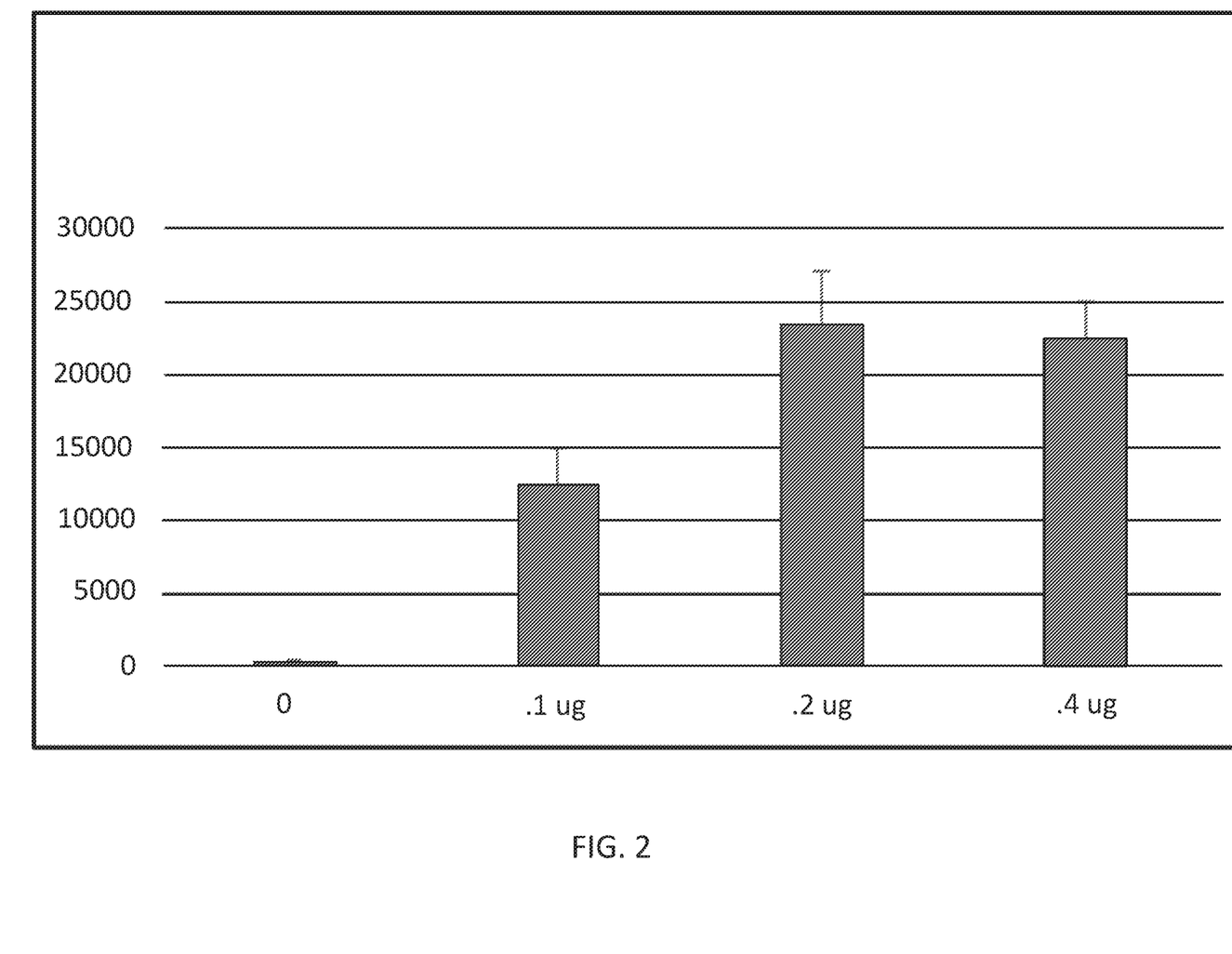
FIG. 2 shows stimulation of HUVEC proliferation.

Fibroblast derived exosomes were obtained as described in Example 1 and added to cultures of human umbilical vein endothelial cells (HUVEC). Cells were incubated for 48 hours and proliferation was assessed by thymidine incorporation assay. In FIG. 2, proliferation is expressed as counts per minute (CPM).

Example 3

Prevention of Limb Loss in Critical Limb Ischemia Mouse Model

BALB/c mice were treated by femoral artery ligation and local nerve injury in a previously published model (Meng et al., 2007, J. Trans. Med. 5:57).

Exosomes were prepared from the cell culture supernatant of day 4 foreskin fibroblast cultures by differential centrifugation. Briefly, recovered culture supernatant was subjected to three successive centrifugations at 300 g (5 min), 1,200 g (20 min), and 10,000 g (30 min) to eliminate cells and debris, followed by centrifugation for 1 h at 100,000 g. To remove excess serum proteins, the exosome pellet was washed with a large volume of PBS, centrifuged at 100,000 g for 1 h, and finally resuspended in 120 µl of PBS for further studies. The exosomes were quantified by a micro Bradford protein assay (Bio-Rad). Each batch was standardized by protein content.

Mice were administered 5 micrograms of fibroblast exosomes in a volume of 100 microliters 3 days after femoral artery ligation (treated). Controls where administered 5 micrograms of fetal calf serum derived exosomes (untreated). Limb loss was present in all the untreated mice (7/7), whereas it was observed in only 1/7 treated mice. Administration of mesenchymal stem cell exosomes did not result in limb salvage by day 35.

| Mouse Number | Day 7 | Day 14 | Day 21 | Day 28 | Day 35 |
| --- | --- | --- | --- | --- | --- |
| 1 Control | | | | | Limb Loss |
| 2 Control | | | Limb Loss | | |
| 3 Control | | | Limb Loss | | |
| 4 Control | | | | Limb Loss | |
| 5 Control | | | | Limb Loss | |
| 6 Control | | | | Limb Loss | |
| 7 Control | | | | | Limb Loss |
| 8 Treated | | | | | |
| 9 Treated | | | | | |
| 10 Treated | | | | | |
| 11 Treated | | | | | Limb Loss |
| 12 Treated | | | | | |
| 13 Treated | | | | | |
| 14 Treated | | | | | |

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications cited herein are hereby incorporated by reference in their entirety herein.

1. Thery, C., M. Ostrowski, and E. Segura, Membrane vesicles as conveyors of immune responses. Nature reviews. Immunology, 2009. 9(8): p. 581-93.
2. Ludwig, A.K. and B. Giebel, Exosomes: Small vesicles participating in intercellular communication. The international journal of biochemistry & cell biology, 2011.
3. Alvarez-Erviti, L., et al., Lysosomal dysfunction increases exosome-mediated alpha-synuclein release and transmission. Neurobiology of disease, 2011. 42(3): p. 360-7.
4. Silverman, J.M. and N.E. Reiner, Exosomes and other microvesicles in infection biology: organelles with unanticipated phenotypes. Cellular microbiology, 2011. 13(1): p. 1-9.
5. Pan, B.T. and R.M. Johnstone, Fate of the transferrin receptor during maturation of sheep reticulocytes in vitro: selective externalization of the receptor. Cell, 1983. 33(3): p. 967-78.
6. Alonso, R., et al., Diacylglycerol kinase alpha regulates the formation and polarisation of mature multivesicular bodies involved in the secretion of Fas ligand-containing exosomes in T lymphocytes. Cell death and differentiation, 2011. 18(7): p. 1161-73.
7. Zhang, H., et al., CD4(+) T cell-released exosomes inhibit CD8(+) cytotoxic T-lymphocyte responses and antitumor immunity. Cellular & molecular immunology, 2011. 8(1): p. 23-30.
8. Mathews, J.A., et al., CD23 Sheddase A disintegrin and metalloproteinase 10 (ADAM10) is also required for CD23 sorting into B cell-derived exosomes. The Journal of biological chemistry, 2010. 285(48): p. 37531-41.
9. Buschow, S. I., et al., MHC class II-associated proteins in B-cell exosomes and potential functional implications for exosome biogenesis. Immunology and cell biology, 2010. 88(8): p. 851-6.
10. Hwang, I. and D. Ki, Receptor-mediated T cell absorption of antigen presenting cell-derived molecules. Frontiers in bioscience: a journal and virtual library, 2011. 16: p. 411-21.
11. Viaud, S., et al., Updated technology to produce highly immunogenic dendritic cell-derived exosomes of clinical grade: a critical role of interferon-gamma. Journal of immunotherapy, 2011. 34(1): p. 65-75.
12. Clayton, A., et al., Cancer exosomes express CD39 and CD73, which suppress T cells through adenosine production. Journal of immunology, 2011. 187(2): p. 676-83.
13. Battke, C., et al., Tumour exosomes inhibit binding of tumour-reactive antibodies to tumour cells and reduce ADCC. Cancer immunology, immunotherapy: CII, 2011. 60(5): p. 639-48.
14. Lachenal, G., et al., Release of exosomes from differentiated neurons and its regulation by synaptic glutamatergic activity. Molecular and cellular neurosciences, 2011. 46(2): p. 409-18.
15. Faure, J., et al., Exosomes are released by cultured cortical neurones. Molecular and cellular neurosciences, 2006. 31(4): p. 642-8.
16. Fitzner, D., et al., Selective transfer of exosomes from oligodendrocytes to microglia by macropinocytosis. Journal of cell science, 2011. 124(Pt 3): p. 447-58.
17. Mincheva-Nilsson, L. and V. Baranov, The role of placental exosomes in reproduction. American journal of reproductive immunology, 2010. 63(6): p. 520-33.

What is claimed is:

1. A method of stimulating angiogenesis in an individual, comprising the step of administering to the individual an effective amount of fibroblast-derived exosomes or one or more biologically active fractions thereof.

2. The method of claim 1, further comprising the steps of: a) obtaining one or more fibroblast cells; b) culturing said fibroblast cells in a culture under conditions to allow for production of exosomes into culture media; c) extracting exosomes from said culture media; and d) administering said extracted exosomes or one or more biologically active fractions thereof into an individual in need of angiogenesis.

3. The method of claim 1, wherein said fibroblasts are derived from a biopsy.

4. The method of claim 1, wherein the fibroblasts are from the individual.

5. The method of claim 1, wherein the fibroblasts are not from the individual.

6. The method of claim 1, wherein said fibroblasts are cultured in a media allowing for fibroblast proliferation.

7. The method of claim 6, wherein said media allowing for fibroblast proliferation comprises one or more factors that are mitogenic for fibroblasts.

8. The method of claim 7, wherein said factors that are mitogenic for fibroblasts include one or more factors selected from the group comprising of: a) FGF-1; b) FGF-2; c) FGF-5; d) EGF; e) CNTF; f) KGF-1; g) PDGF; h) platelet rich plasma; i) TGF-alpha; j) HGF-1; and (k) a combination thereof.

9. The method of claim 1, wherein said fibroblasts are cultured under hypoxia.

10. The method of claim 1, wherein the exosomes are collected from fibroblasts while said fibroblasts are in a proliferating state.

11. The method of claim 1, wherein said exosomes are collected from fibroblasts while said fibroblasts are cultured in a media comprising no proliferation-inducing factors or in media that comprise reduced levels of said proliferation-inducing growth factors compared to standard levels.

12. The method of claim 1, wherein said exosomes are collected from said fibroblasts that have been cultured in 2-8% oxygen for at least 1 day.

13. The method of claim 12, wherein the cells are cultured for 1-15 days.

14. The method of claim 12, wherein the cells are cultured for 5-10 days.

15. The method of claim 1, wherein the cells are passaged for at least 1 passage.

16. The method of claim 1, wherein said exosomes are in a preparation, said preparation comprising less than 5% polyethylene glycol.

17. The method of claim 1, wherein the exosomes are purified using polyethylene glycol.

18. The method of claim 1, wherein the exosomes are purified using ultrafiltration.

19. The method of claim 17, wherein polyethylene glycol is added to the exosomes after purification.

20. The method of claim 1, wherein said exosomes express markers selected from a group consisting of (a) CD63; (b) CD9; (c) MHC I; (d) CD56; and (e) a combination thereof.

21. The method of claim 1, wherein the extracting step comprises anion exchange chromatography under high pressure.

22. The method of claim 21, wherein support for the anion exchange chromatography is functionalized with quaternary amines.

23. The method of claim 21, wherein support for the anion exchange chromatography is in the form of beads.

24. The method of claim 1, wherein the extracting step comprises gel permeation chromatography.

25. The method of claim 15, wherein the gel permeation chromatography occurs after the anion exchange chromatography.

26. The method of claim 24, wherein the gel permeation chromatography occurs before the anion exchange chromatography.

27. The method of claim 1, wherein the extracting step further comprises an enrichment step for the exosomes.

28. The method of claim 27, wherein the enrichment step comprises one or more of centrifugation, clarification, filtration, concentration, and/or ultrafiltration.

29. The method of claim 1, wherein the extracting step further comprises non-specific affinity chromatography.

30. The method of claim 1, wherein the extracting step further comprises filtration.

31. The method of claim 1, wherein the individual is at risk for limb loss, has ischemic heart disease, ischemic brain disease, has a gastrointestinal ulcer, and/or is in need of wound repair.

32. The method of claim 31, wherein the individual in need of wound repair has diabetes.

* * * * *